US00PP15508P3

(12) United States Plant Patent
Wolfram

(10) Patent No.: US PP15,508 P3
(45) Date of Patent: Feb. 1, 2005

(54) *PRUNUS* TREE ROOTSTOCK NAMED 'PIKU 3'

(50) Latin Name: *Prunus L.*
Varietal Denomination: Piku 3

(75) Inventor: Brigitte Wolfram, Dresden (DE)

(73) Assignee: Consortium Deutscher Baumschulen GmbH, Ellerbek (DE)

( * ) Notice: Subject to any disclaimer, the term of this patent is extended or adjusted under 35 U.S.C. 154(b) by 16 days.

(21) Appl. No.: 10/136,839

(22) Filed: May 1, 2002

(65) Prior Publication Data

US 2003/0208809 P1 Nov. 6, 2003

(51) Int. Cl.[7] ..... A01H 5/00

(52) U.S. Cl. ..... Plt./183

(58) Field of Search ..... Plt./183

*Primary Examiner*—Anne Marie Grunberg
*Assistant Examiner*—Annette H Para

(74) *Attorney, Agent, or Firm*—Webb Ziesenheim Logsdon Orkin & Hanson, P.C.

(57) ABSTRACT

A new and distinct *Prunus* rootstock compatible with other *Prunus* varieties and producing trees with reduced growth, adaptability to soil and high productivity.

4 Drawing Sheets

Classification: *Prunus L.*
Varietal denomination: 'Piku 3'.

BACKGROUND OF THE INVENTION

The present invention comprises a new and distinct cultivar of hybrid *Prunus* known by the varietal name 'Piku 3'. The new variety was discovered in 1972 in a selective breeding program designed to produce growth reducing rootstock for cherry trees in Dresden-Pillnitz, Germany as a cross between an unnamed, unpatented variety of *Prunus pseudocerasus* (female parent) and an unnamed, unpatented *Prunus* hybrid of *Prunus canescens*×*Prunus incisa* (male parent). The new variety differs from its parents in its growth habit. The following characteristic distinguish the new variety from *Prunus avium* rootstock varieties:

1. Three-way hybrid.
2. Reduces growth in grafted varieties by 20%.
3. Minimally precocious crop.
4. Adaptable to soil.

The new variety was first asexually reproduced via green cuttings in 1975 in Dresden-Pillnitz, Germany and subsequent propagation therein has confirmed that the characteristics of the new variety are stable and are transmitted to subsequent generations.

DESCRIPTION OF THE DRAWINGS

The accompanying photographic drawings illustrate the new variety, with the color being as nearly true as is possible with color illustrations of this type.

DESCRIPTION OF THE PLANT

Figure 1:
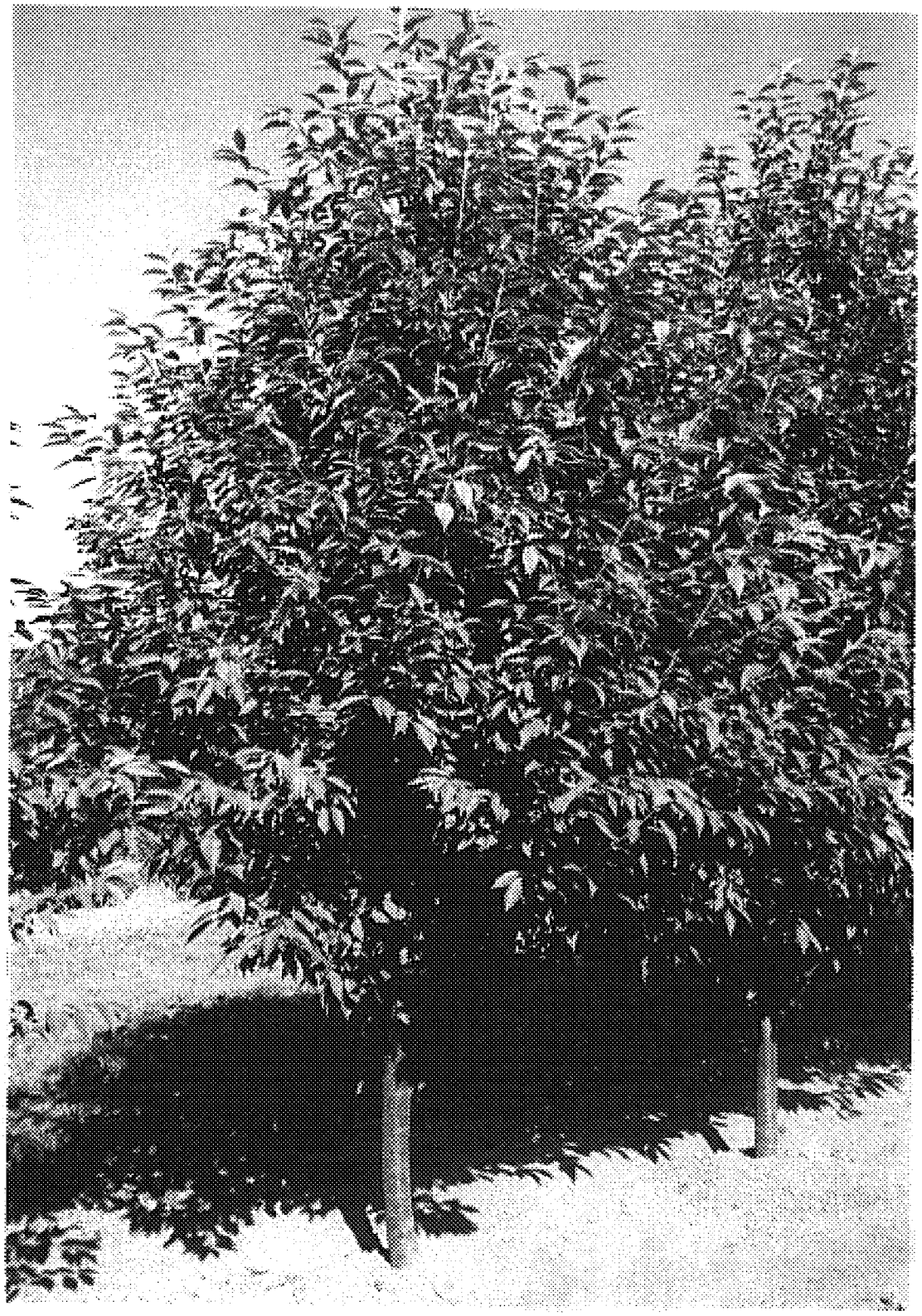
FIG. 1 shows the tree of the new variety.
Figure 2:
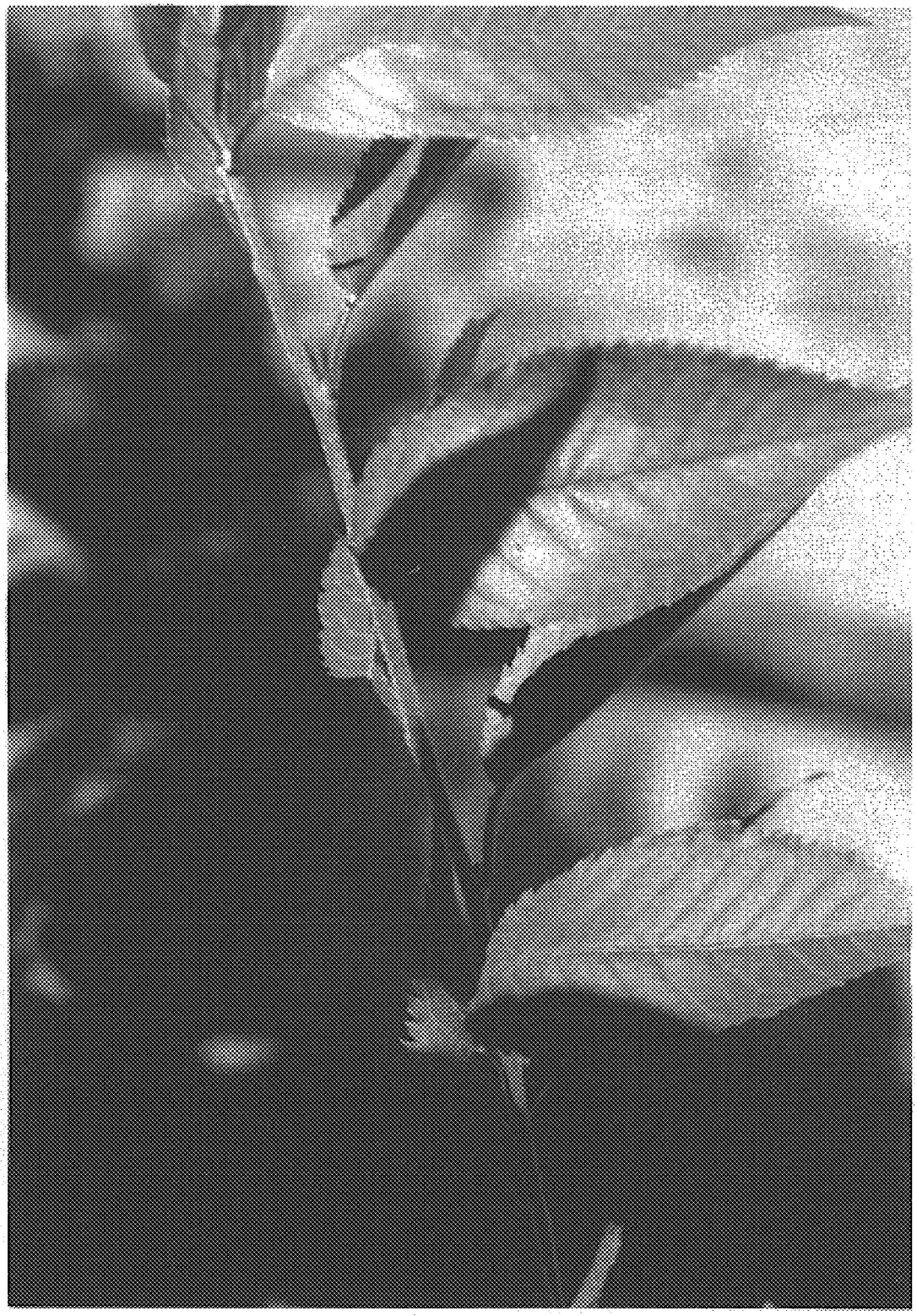
FIG. 2 shows a branch with leaves.
Figure 3:
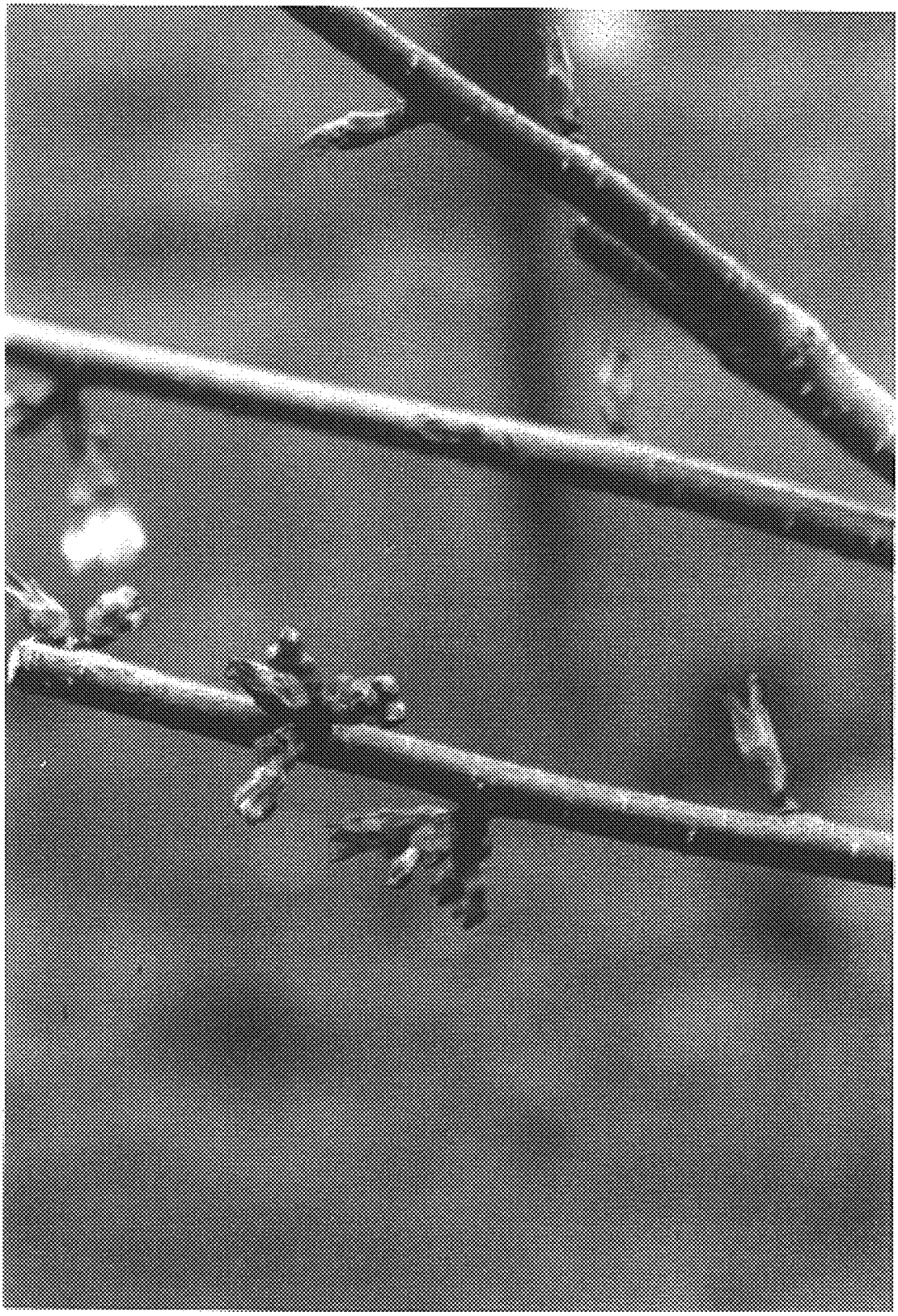
FIG. 3 shows a branch with flower buds.
Figure 4:
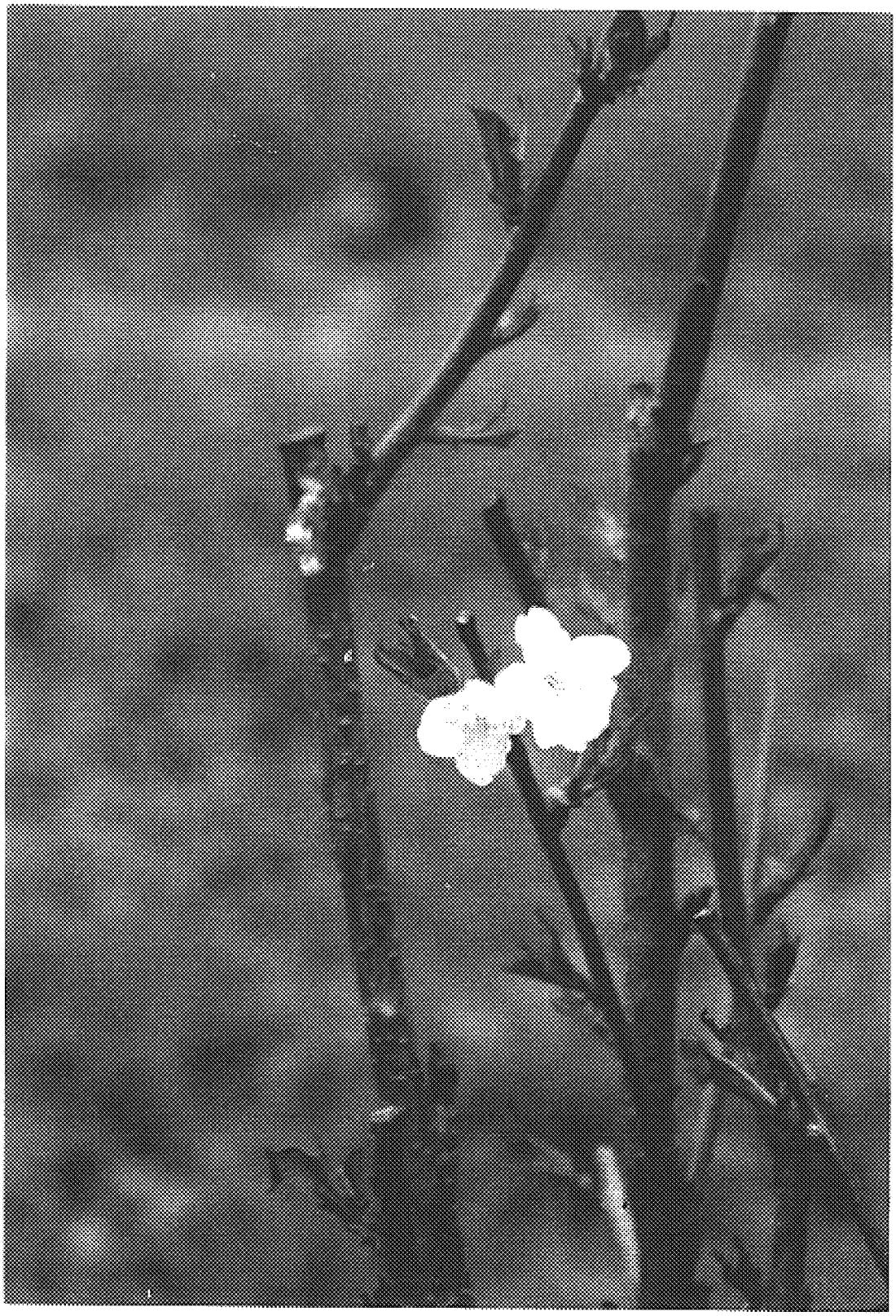
FIG. 4 shows a branch with opened flowers.

The following detailed description sets forth the characteristics of the new cultivar. The data which defines these characteristics were collected by asexual reproductions via green cuttings carried out in Dresden-Pillnitz, Germany. The color designations were taken outdoors in Dresden-Pillnitz, Germany. Rootstocks were 6 to 7 years old when described. Color designations are noted with reference to standard *Prunus avium* rootstock. The new variety is adaptable to soil and is free of PNRV and PDV. As a rootstock, it can be reproduced via softwood cuttings and tissue culture. The new variety anchors well with some root sprouts, has good compatibility with grafts and exhibits growth reduction.

TREE

Size: Average height of 3.0 m and an average width of 1.90 m.
Form: Upright, pyramidal.
Trunk:
- *Bark color.*—Brown.
- *Diameter.*—8.1 cm, measured at a height of 40 cm.

Branches:
- *Surface texture.*—Pubescent.
- *Bark color.*—200C.
- *New growth color.*—Light-green red.
- *Mature growth color.*—Dark.
- *Average crotch angle.*—40–45°.
- *Internode length.*—About 2.3 cm.
- *Lenticels.*—Diameter: 0.10–0.20 cm. Color: 160A. Amount per shoot: >100.
- *Bud.*—Small.

Leaves:
- *Length.*—8.7 cm.
- *Width.*—4.0 cm.
- *Surface texture.*—Pubescent.
- *Shape.*—Elliptical.
- *Color.*—Upper Surface: 137A. Lower Surface: 146A.

Petioles:
- *Length.*—1.2 cm.
- *Thickness.*—0.10 cm.

Leaf glands:
*Quantity.*—1–2.
*Position.*—Under leaf end.
*Size.*—0.10–0.15 cm.
*Color.*—Green.
Stipules:
*Quantity.*—Rare.
*Length.*—0.6–1.5 cm.
*Color.*—Green.
Flowers:
*Diameter.*—2.70 cm.
*Color.*—Upper Surface: N155A. Lower Surface: N155A.
*Bud color.*—69C.
*Number.*—Many.
*Petals.*—Length: Approximately 1.2 cm. Width: Approximately 0.6 cm. Quantity per flower: 5.
*Sexual characteristics.*—Diploid.
*Stamen number.*—>10.
*Pistil number.*—1.

FRUIT

Maturity date/location: Mid-season in Dresden, Pillnitz.
Size: Small; low crop yield.
Weight: 1–2 grams.
Axial diameter: 1–2 cm.
Fruit stone:
*Length.*—Approximately 0.7 cm.
*Diameter.*—Approximately 0.4 cm.
Skin: Thin, soft, colored 183A/183B.
Flesh color: 187A.

GENERAL

Weather hardiness: Moderately susceptible to winter frost.
Disease resistance: Tolerant to Cytospora.

I claim:

1. A new and distinct variety of *Prunus* rootstock tree named 'Piku 3' substantially as shown and described.

* * * * *